(12) United States Patent
Takamine et al.

(10) Patent No.: US 10,345,275 B2
(45) Date of Patent: *Jul. 9, 2019

(54) STRUCTURE EVALUATION SYSTEM, STRUCTURE EVALUATION APPARATUS, AND STRUCTURE EVALUATION METHOD

(71) Applicants: KABUSHIKI KAISHA TOSHIBA, Tokyo (JP); Kyoto University, Kyoto-shi, Kyoto (JP)

(72) Inventors: Hidefumi Takamine, Tokyo (JP); Kazuo Watabe, Kanagawa (JP); Tomoki Shiotani, Kyoto (JP)

(73) Assignees: KABUSHIKI KAISHA TOSHIBA, Tokyo (JP); KYOTO UNIVERSITY, Kyoto-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/455,646

(22) Filed: Mar. 10, 2017

(65) Prior Publication Data

US 2017/0363587 A1 Dec. 21, 2017

Related U.S. Application Data

(63) Continuation of application No. PCT/JP2017/008824, filed on Mar. 6, 2017.

(30) Foreign Application Priority Data

Jun. 15, 2016 (JP) ................................. 2016-119306

(51) Int. Cl.
*G01N 29/04* (2006.01)
*G01N 29/06* (2006.01)
(Continued)

(52) U.S. Cl.
CPC ....... *G01N 29/4463* (2013.01); *G01N 29/043* (2013.01); *G01N 29/045* (2013.01);
(Continued)

(58) Field of Classification Search
CPC ............... G01N 29/14; G01N 29/2437; G01N 29/4463; G01N 29/2475; G01N 2291/0232; G01N 2291/0289
See application file for complete search history.

(56) References Cited

U.S. PATENT DOCUMENTS

2014/0060193 A1 3/2014 Zhu et al.
2014/0067284 A1 3/2014 Breed
(Continued)

FOREIGN PATENT DOCUMENTS

CN 102269736 B 12/2012
JP 2004-125721 A 4/2004
(Continued)

OTHER PUBLICATIONS

Zhang et al., Multisensor Data Fusion for Impact-Echo Testing of Concrete Structures, Smart Materials and Structures 21 (2012).
(Continued)

*Primary Examiner* — Bryan Bui
(74) *Attorney, Agent, or Firm* — Oblon, McClelland, Maier & Neustadt, L.L.P.

(57) ABSTRACT

According to an embodiment, a structure evaluation system includes a plurality of sensors, a position locator, and an evaluator. The sensors detect an elastic wave generated from a structure. The position locator derives a source distribution of the elastic waves generated from the structure, caused by an impact on the structure. The evaluator evaluates a state of deterioration of the structure from characteristic parameters of the elastic waves in the source distribution.

12 Claims, 7 Drawing Sheets

(51) Int. Cl.
*G01N 29/14* (2006.01)
*G01N 29/24* (2006.01)
*G01N 29/44* (2006.01)

(52) U.S. Cl.
CPC .......... *G01N 29/069* (2013.01); *G01N 29/14* (2013.01); *G01N 29/2437* (2013.01); *G01N 29/2475* (2013.01); *G01N 2291/0232* (2013.01); *G01N 2291/0258* (2013.01); *G01N 2291/0289* (2013.01)

(56) References Cited

U.S. PATENT DOCUMENTS

| | | |
|---|---|---|
| 2016/0139084 A1 | 5/2016 | Usui et al. |
| 2017/0336364 A1 | 11/2017 | Watabe et al. |
| 2017/0336365 A1 | 11/2017 | Watabe et al. |
| 2017/0363586 A1* | 12/2017 | Takamine ............ G01N 29/043 |

FOREIGN PATENT DOCUMENTS

| | | |
|---|---|---|
| JP | 2011-242269 A | 12/2011 |
| JP | 2014-95555 A | 5/2014 |
| JP | 2015-31630 A | 2/2015 |
| JP | 2016-99119 A | 5/2016 |
| WO | WO 2015/182079 A1 | 12/2015 |

OTHER PUBLICATIONS

Mazzeo et al., "Acoustic Impact-Echo Investigation of Concrete Delaminations Using Liquid Droplet Excitation," 51 NDT&E International 41-44, (2012).

Grosse et al., "Acoustic Emission Testing," Basics for Research-Applications in Civil Engineering (2008).

Ito et al., "Nondestructive Testing Method of Concrete Using Impact Acoustics," 30 NDT&E International 4 (1997).

Schabowicz, Ultrasonic Tomography—The latest Nondestructive Technique for Testing Concrete Members—Description, Test Methodology, Application Example, 14 Archives of Civil and Mechanical Engineering 295-303 (2014).

* cited by examiner

STRUCTURE EVALUATION SYSTEM, STRUCTURE EVALUATION APPARATUS, AND STRUCTURE EVALUATION METHOD

TECHNICAL FIELD

The present invention relates to a structure evaluation system, a structure evaluation apparatus, and a structure evaluation method.

BACKGROUND ART

When load is applied to a concrete floor slab of a bridge due to traffic or the like. Acoustic Emission (AE) occurs due to crack propagation, friction, or the like in the floor slab. AE can be detected by installing an AE sensor on a surface of the floor slab. AE is an elastic wave generated as a fatigue crack of a material develops. Further, by installing a plurality of AE sensors, a source location of the elastic wave (hereinafter referred to as "AE source") can be calculated from a difference in AE arrival time between the sensors.

Generally, in a concrete floor slab of a bridge, although damage inside the floor slab such as horizontal cracks is very difficult to detect by conventional nondestructive inspection, the damage inside can be estimated by analyzing data acquired by the AE sensors. However, a large amount of time is required for installing an AE sensor in a bridge and the like and obtaining sufficient data for estimating damage thereto. Therefore, an inside of concrete cannot be evaluated efficiently in some cases. Such a problem is not limited to the concrete floor slab of a bridge but is a problem common to all the structures in which elastic waves are generated as cracks occur or develop.

CITATION LIST

Patent Literature

[Patent Literature 1]
Japanese Unexamined Patent Application, First Publication No. 2004-125721

SUMMARY OF INVENTION

Technical Problem

An objective of the present invention is to provide a structure evaluation system, a structure evaluation apparatus, and a structure evaluation method capable of efficiently evaluating a structure.

Solution to Problem

According to an embodiment, a structure evaluation system includes a plurality of sensors, a position locator, and an e valuator. The sensors detect an elastic wave generated from a structure. The position locator derives a source distribution of the elastic waves generated from the structure, caused by an impact on the structure. The evaluator evaluates a state of deterioration of the structure from characteristic parameters of the elastic waves in the source distribution.

DESCRIPTION OF EMBODIMENTS

Hereinafter, a structure evaluation system, a structure evaluation apparatus, and a structure evaluation method according to an embodiment will be described with reference to the accompanying drawings.

Figure 1:
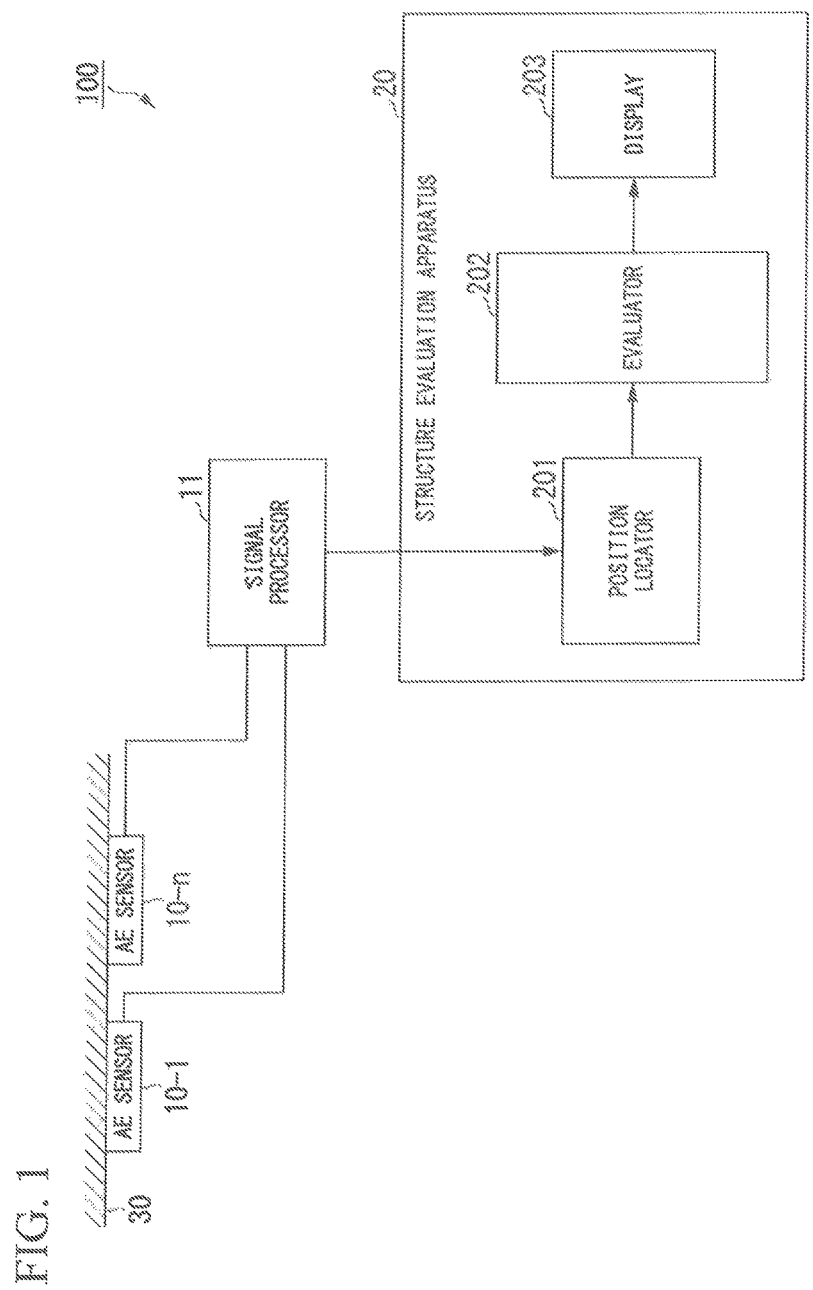
FIG. 1 is a view illustrating a system constitution of a structure evaluation system 100 according to an embodiment.

FIG. 1 is a view illustrating a system constitution of a structure evaluation system 100 according to an embodiment. The structure evaluation system 100 is used for evaluating the soundness of a structure. In the embodiments, the term evaluation refers to determining a degree of soundness of a structure, or a state of deterioration of the structure, based on a standard or standards. Although a bridge is described as an example of a structure in the embodiment, a structure is not necessarily limited to a bridge. For example, a structure may be any structure as long as an elastic wave is generated in the structure due to occurrence or development of cracks or an external impact (e.g., rain, artificial rain, etc.). Also, a bridge is not limited to a structure constructed over a river or a valley, and includes various structures provided above the ground (e.g., an elevated bridge over a highway).

The structure evaluation system 100 includes a plurality of acoustic emission (AE) sensors 10-1 to 10-$n$ (n is an integer equal to or greater than 2), a signal processor 11, and a structure evaluation apparatus 20. The signal processor 11 and the structure evaluation apparatus 20 are connected to be able to communicate via a wire or wirelessly. Further, in the description below, the AE sensors 10-1 to 10-$n$ are referred to as an AE sensor 10 when not distinguished.

The AE sensor 10 is installed in a structure. For example, the AE sensor 10 is installed on a concrete floor slab 30 of a bridge. The AE sensor 10 has a piezoelectric element, detects an elastic wave (AE wave) generated by the structure, and converts the detected elastic wave into a voltage signal (AE source signal). The AE sensor 10 performs processing such as amplification and frequency limiting on the AE source signal and outputs the processing result to the signal processor 11. Instead of the AE sensor 10, an acceleration sensor can be used. In this case, the acceleration sensor performs processing similar to the processing by the AE sensor 10 to generate a processed signal and output the processed signal to the signal processor 11. The thickness of a concrete slab is at least 15 cm.

The signal processor 11 receives the AE source signal processed by the AE sensor 10 as an input. The signal processor 11 performs necessary signal processing such as noise removal and parameter extraction on the input AE source signal to extract an AE parameters including information on the elastic wave. The information on the elastic wave is, for example, information such as an amplitude, an energy, a rise time, a duration, a frequency, and a zero-crossing count number of the AE source signal. The signal processor 11 outputs information based on the extracted AE parameters to the structure evaluation apparatus 20 as an AE signal. The AE signal output from the signal processor 11 includes information such as a sensor ID, an AE detection time, an AE source signal amplitude, an energy, a rise time, and a frequency.

Here, the amplitude of the AE source signal is, for example, a value of the maximum amplitude among elastic waves. The energy is, for example, a value obtained by time integration of squared amplitude at each time point. The definition of energy is not limited to the above example, and may be, for example, one approximated by using an envelope curve of a waveform. The rise time is, for example, a time T1 until an elastic wave rises above a preset predetermined value from zero. The duration is, for example, an amount of time from the start of the rise of an elastic wave until the amplitude becomes smaller than a preset value. The frequency is a frequency of an elastic wave. The zero-crossing count number is, for example, the number of times that an elastic wave crosses a reference line passing a zero value.

The structure evaluation apparatus 20 includes a central processing unit (CPU), a memory, an auxiliary storage device or the like connected via a bus, and executes an evaluation program. By executing the evaluation program, the structure evaluation apparatus 20 functions as an apparatus including a position locator 201, an evaluator 202, and a display 203. Further, all or some of the functions of the structure evaluation apparatus 20 may be realized by using hardware such as an application specific integrated circuit (ASIC), a programmable logic device (PLD), a field programmable gate array (FPGA), or the like. Also, the evaluation program may be recorded in a computer-readable recording medium. The computer-readable recording medians is, for example, a portable medium such as a flexible disk, a magneto-optical disk, a read-only memory (ROM), a compact disc (CD)-EOM or the like, or a storage device such as a hard disk embedded in a computer system. Also, the evaluation program may be transmitted and received via an electric communication line.

The position locator 201 receives an AE signal output from the signal processor 11 as an input. Also, the position locator 201 pre-stores information on an installation position of the AE sensor 10 in the structure (hereinafter referred to as "sensor position information") by associating the information to a sensor ID. The information on the installation position is, for example, latitude and longitude, or a distance in the horizontal direction and the vertical direction from a specific position on the structure, and the like. The position locator 201 locates a position of an AE source on the basis of the information such as the sensor ID and she AE detection time included in the input AE signal and the pre-stored sensor position information. For example, the position locator 201 uses a plurality of AE signals caused by an impact on the structure to locate the AE source. Here, the impact on the structure is an impact generated due to colliding of numerous micro-objects. The plurality of AE signals caused by an impact on the structure are signals which axe obtained from elastic waves generated at the structure, where the elastic waves have been generated by impacts caused by collisions of numerous micro-objects to the structure. The numerous micro-objects are objects providing influence to the structure from outside of the structure. For example, the numerous micro-objects am objects generated by weather phenomena such as raindrops, hail and snow pellets. Also, the position locator 201 derives a source distribution by using the position location results. The source distribution represents the distribution of AE sources generated from the structure. The position locator 201 outputs the derived source distribution to the evaluator 202.

The evaluator 202 receives the source distribution output from the position locator 201 as an input. The evaluator 202 evaluates the soundness of the structure on the basis of the input source distribution. For example, the evaluator 202 evaluates a state of deterioration of the structure front characteristic parameters of the elastic waves in the source distribution. The characteristic parameters of the elastic waves in the source distribution may be, but not limited to, a density of the AE sources. As an example of the processing, on the basis of the source distribution, the evaluator 202 may evaluate a region in which the density of the AE sources is less than a first threshold value as a region in which deterioration of the structure is occurring. The evaluator 202 makes the display 203 display the evaluation result. The first threshold value may be set in advance or may be appropriately set.

The display 203 is an image display device such as a liquid crystal display or an organic electro luminescence (EL) display. The display 203 displays the evaluation result according to the control of the evaluator 202. The display 203 may be an interface for connecting the image display device to the structure evaluation apparatus 20. In this case, the display 203 generates a video signal for displaying the evaluation result, and outputs the video signal to the image display device connected to the display 203.

Figure 2:
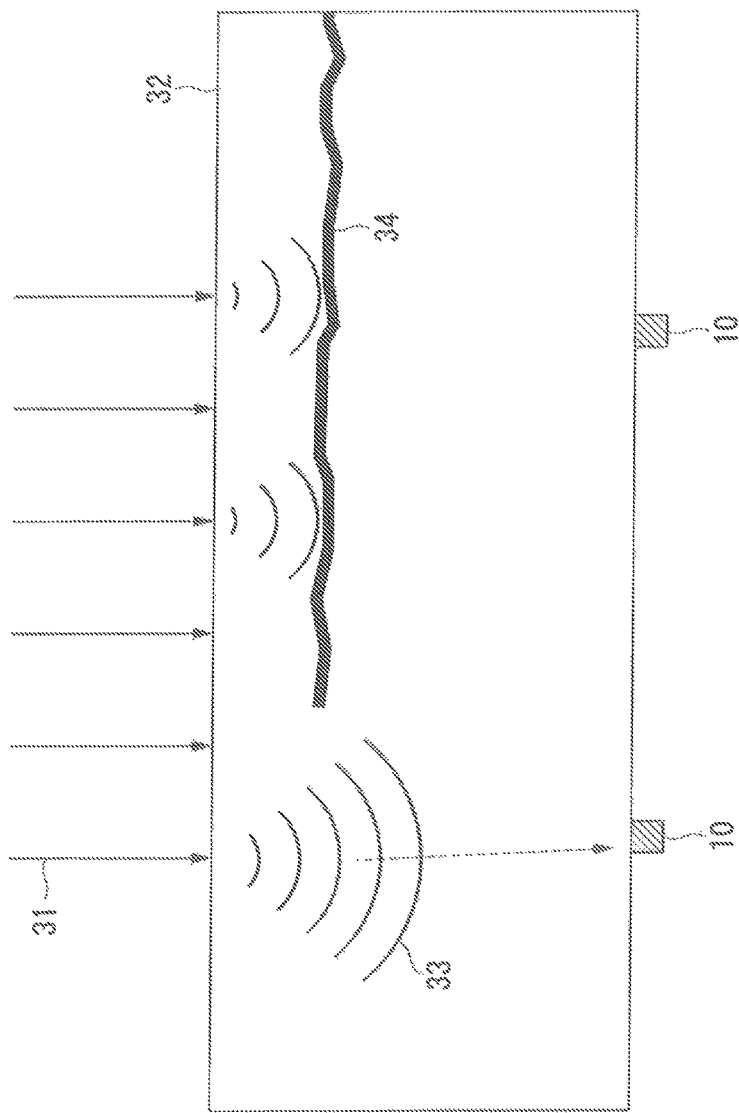
FIG. 2 is a view illustrating a state of propagation of an elastic wave due to rainfall.

FIG. 2 is a view illustrating a state of propagation of an elastic wave due to rainfall. As illustrated in FIG. 2, when a raindrop 31 collides with a road surface 32, an elastic wave 33 is generated at the collision position. The elastic wave 33 propagates through the interior of the floor slab and also to a lower surface thereof. The elastic wave 33 that maintains a sufficient amplitude until reaching the AE sensor 10 installed at the lower surface is detected by the AE sensor 10. As in the case of the elastic wave 33 due to damage, the position locator 201 can identify an approximate collision position of the raindrop 31 by locating a position with respect to the elastic wave 33 generated by rain. In this way, an impact caused by collision of a micro-object is an impact applied to a surface (the road surface 32 in FIG. 2) opposite to the surface at which the AE sensor is installed.

However, when a large horizontal crack 34 is present inside the floor slab, the elastic wave 33 generated by the raindrop 31 colliding with the road surface 32 is blocked by the crack, or bypasses or is attenuated by the crack. Therefore, it is difficult for the elastic wave 33 having a sufficient amplitude to reach the AE sensor 10 located directly below the crack. Consequently, the position locator 201 locates fewer AE sources in the area under the large horizontal crack 34. Collision of the raindrops 31 against the road surface 32 due to rainfall occurs randomly and evenly with respect to the entire region. Therefore, the elastic wave 33 is detected on the lower surface of the floor slab without large damage, and AE sources are evenly located all over a region when the position location of the AE sources is performed. On the other band, when the inside of the floor slab has huge damage, it is assumed that the density of the AE sources directly below the damaged portion is reduced. The structure evaluation apparatus 20 in the embodiment evaluates the soundness of the structure on the basis of such assumption.

Figure 3:
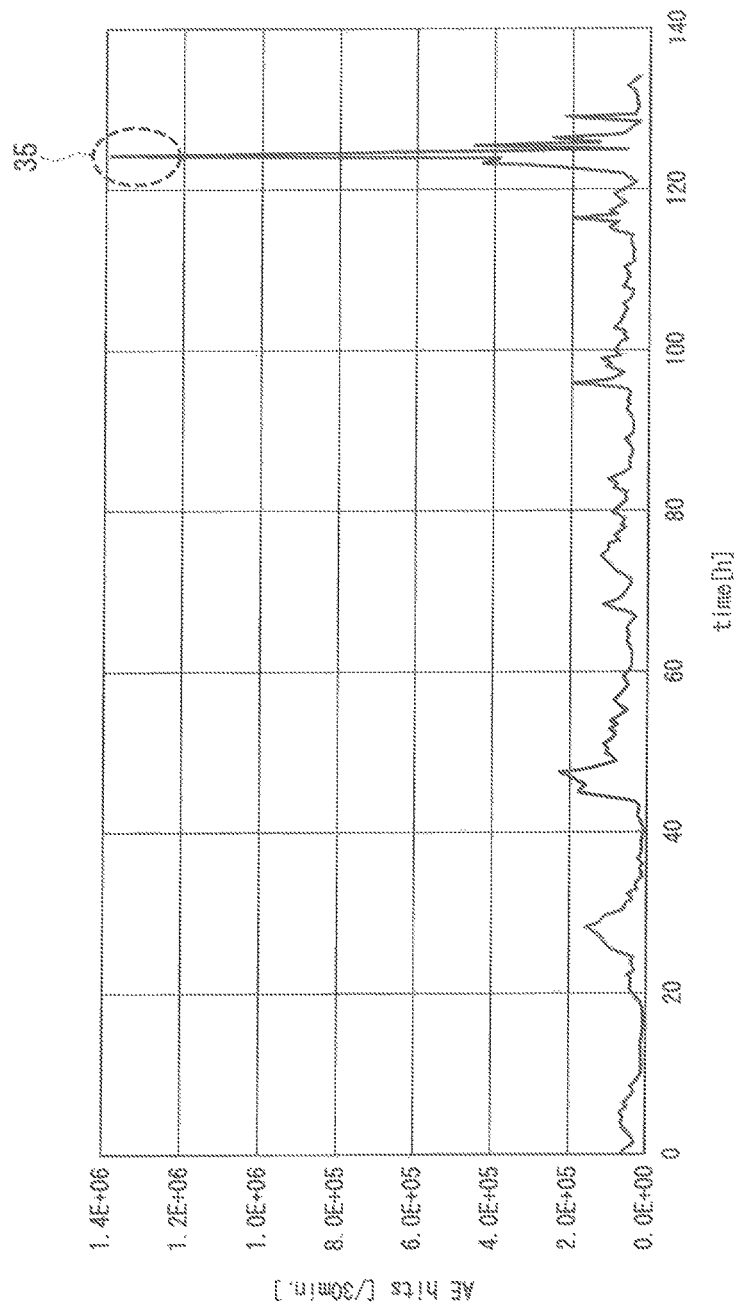
FIG. 3 is a view illustrating a tread of the number of occurrences of elastic waves during a certain measurement period.

FIG. 3 is a view illustrating a trend of the number of occurrences of elastic waves during a certain measurement period. In FIG. 3, the horizontal axis represents the time (hours) during the measurement period, and the vertical axis represents the number of hits. The number of hits is the number of detected elastic waves. The number of hits represents the number of detected elastic waves every 30 minutes, for example. In FIG. 3, the number of hits from 0 hours to 120 hours in the measurement period is the number of detected elastic waves in the normal state. With respect to the number of hits during the measurement period from 120 hours to 140 hours, a period in which a large number of elastic waves 35 are observed as compared with the number of occurrences of elastic waves at the normal time (measurement period from 0 hours to 120 hours) is present (reference numeral 35 in FIG. 3). At this time, rainfall with strong wind is observed. In the event of heavy rain such as guerrilla heavy rain, a large amount of elastic waves are generated in such a short time. Since the AE sensor 10 is a very sensitive piezoelectric sensor, the AE sensor 10 also detects elastic waves generated due to factors not caused by damage to the floor slab, such as an impact on the structure due to rain. Thus, rainfall or the like may become a noise source for detection of damage using the AE sensor 10.

On the other hand, the position locator 201 in the structure evaluation apparatus 20 derives the source distribution by using AE signals within a predetermined period including a time at which a large amount of elastic waves are detected (hereinafter referred to as "target time") as illustrated in FIG. 3 as the plurality of AE signals caused by the impact on the structure. Whether a large amount of elastic waves is detected is determined on the basis of whether the number of elastic waves detected at a certain time is a second threshold value or larger. When the number of elastic waves detected at a certain time is the second threshold value or larger, it is determined that a large amount of elastic waves have been detected. On the other hand, when the number of elastic waves detected at a certain time is less than the second threshold value, it is determined that a large amount of elastic waves have not been detected. The second threshold value may be set in advance or may be appropriately set. Further, the predetermined period may be a predetermined period of time before and after a target time (for example, 5 minutes before and after the target time), or may be a period before the target time or a period after the target time when the target time is included in the predetermined period.

Figure 4:
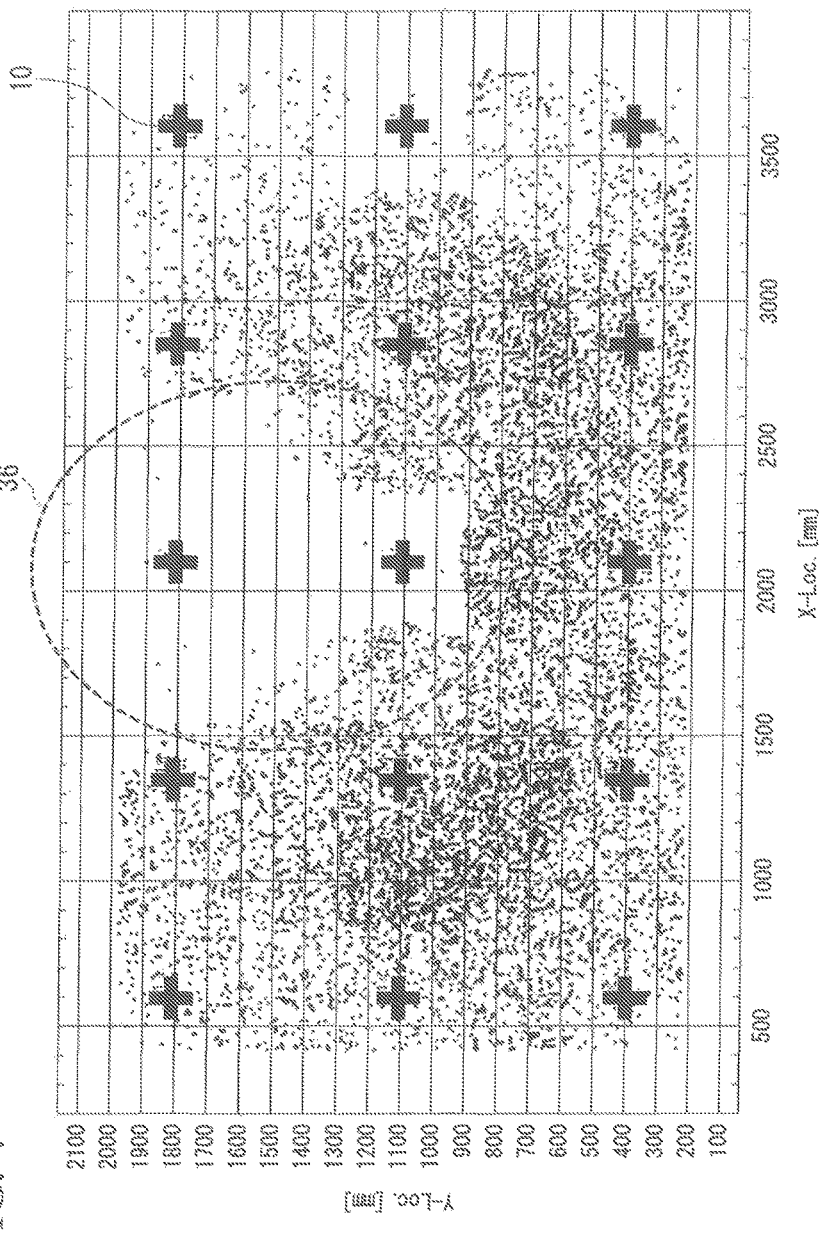
FIG. 4 is a view illustrating an example of a source distribution derived using an AE signal within a predetermined period.

FIG. 4 is a view illustrating an example of a source distribution derived using an AE signal within a predetermined period. In FIG. 4, the horizontal axis and the vertical axis represent the length (mm) in the horizontal direction and the length (mm) in the vertical direction from the specific position on the structure to be evaluated. In FIG. 4, a result of locating AE sources using AE signals during about ten minutes during rainfall in FIG. 3 (e.g., about ten minutes including the time (reference numeral 35) at which a great number of elastic waves 35 are observed in the measurement period from 120 hours to 130 hours) is shown. The + mark in the figure indicates an installation position of the AE sensor 10. While the AE sources am distributed throughout the region of the structure to be evaluated, hardly any of the AE sources are located in a central region 36. The evaluator 202 evaluates a region in which the density of the AE sources is less than the first threshold value (the region 36 in FIG. 4) as a region in which deterioration of the structure is occurring. Any region may be a target for evaluation of the evaluator 202. For example, the evaluator 202 may perform evaluation for each region surrounded by four AE sensors 10, may perform evaluation for each region surrounded by four or more AE sensors 10, may perform evaluation for each region surrounded by three AE sensors 10, or may perform evaluation for each region having a designated range.

Figure 5:
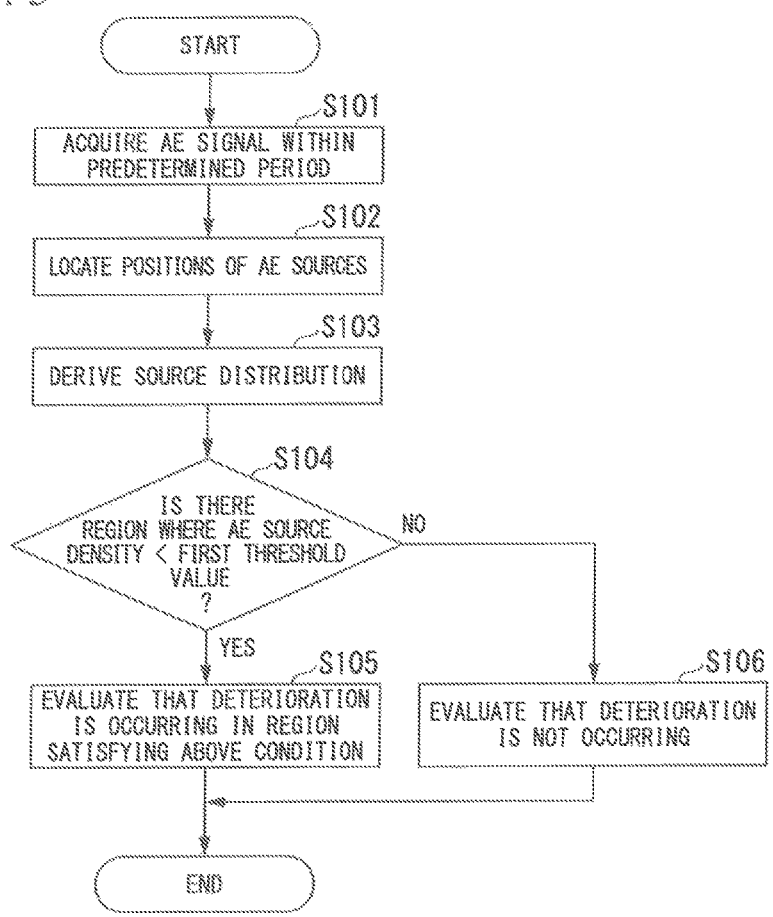
FIG. 5 is a flowchart illustrating a flow of an evaluation process of a structure evaluation apparatus 20.

FIG. 5 is a flowchart illustrating a flow of an evaluation process of the structure evaluation apparatus 20. The process in FIG. 5 is executed when the number of detected elastic waves is the second threshold value or larger. Further, it is assumed that an AE signal output from the signal processor 11 is accumulated in a buffer (not illustrated).

The position locator 201 acquires an AE signal, within a predetermined period from the buffer (not illustrated) (Step S101). That is, the position locator 201 obtains an AE signal within a predetermined period including the target time from the buffer (not illustrated). The position locator 201 locates positions of the AE sources by using a plurality of acquired AE signals (Step S102). Then, the position locator 201 derives the source distribution on the basis of the position location results (Step S103).

The position locator 201 outputs the generated source distribution to the evaluator 202. Using the source distribution output from the position locator 201, the evaluator 202 determines whether a region in which the density of the AE sources is less than the first threshold is present (Step S104). When a region in which the density of the AE sources is less than the first threshold value is present (YES to Step S104), the evaluator 202 evaluates the region in which the density is less than the first threshold value as a region in which deterioration of the structure is occurring (Step S105).

On the other hand, when a region in which the density of the AE sources is less than the first threshold value does not exist (NO to Step S104), the evaluator 202 evaluates that a region in which deterioration of the structure is occurring is not present (Step S106). The evaluator 202 makes the display 203 display the evaluation result. For example, the evaluator 202 displays the evaluation result by displaying a region in which deterioration is occurring in the source distribution in a form different from that of other regions. The form different from that of other regions may include coloring the region in which deterioration is occurring, surrounding the region in which deterioration is occurring by a circle, or marking the region in which deterioration is occurring using a letter. The display 203 displays the evaluation result according to the control of the evaluator 202.

According to the structure evaluation system 100 configured as described above, a structure can be efficiently evaluated. Hereinafter, the effect thereof will be described in detail.

By using the AE signal due to the impact on the structure, the structure evaluation apparatus 20 derives a source distribution including a large amount of AE sources. Then, on the basis of the source distribution, the structure evaluation apparatus 20 evaluates a region in which the density of the AE sources is less than the first threshold value as a region in which the deterioration of the structure is occurring. In this way, by using data which is conventionally a source of noise, a structure can be efficiently evaluated.

Also, the structure evaluation apparatus 20 derives the source distribution by using the AE signal within a predetermined period including the target time as the AE signal caused by the impact on the structure. Conventionally, several tens of hours of measurement is required to perform the evaluation. In comparison with this, according to the method using fee structure evaluation apparatus 20, the required time is significantly shortened by using only the AE signal within the predetermined period including the target time, and the evaluation can be performed efficiently.

Hereinafter, a modified example of the structure evaluation apparatus 20 will be described.

A part or all of the functional units of the structure evaluation apparatus 20 may be provided in separate housings. For example, the structure evaluation apparatus 20 may include only the evaluator 202, and the position locator 201 and the display 203 may be provided in separate housings. In this case, the evaluator 202 acquires the source distribution from another housing and evaluates the soundness of the structure using the acquired source distribution. Then, the evaluator 202 outputs the evaluation result to the display 203 provided in another housing.

By the above constitution, by using an existing device for deriving the source distribution, the manufacturing cost of the structure evaluation apparatus 20 can be suppressed.

The signal processor 11 may be provided in the structure evaluation apparatus 20. In this case, the signal processor 11 acquires an AE source signal processed by the AE sensor 10 directly from the AE sensor 10 or via a relay device (not illustrated).

In FIG. 1, although a single signal processor 11 is connected to the plurality of AE sensors 10-1 to 10-$n$, the structure evaluation system 100 may include a plurality of signal processors 11 and have a plurality of sensor units by the signal processors 11 being connected to the AE sensors 10, respectively.

The evaluator 202 may be configured to derive the source distribution by using the AE signal at the target time as the AE signal caused by an impact on the structure.

Further, the evaluator 202 may operate as an output control unit. The output control unit controls an output unit and outputs the evaluation result. Here, the output unit includes the display 203, a communication unit, and a printing unit. When the output unit is a communication unit, the output control unit controls the communication unit and transmits the evaluation result to another device. Further, when the output unit is a printing unit, the output control unit controls the printing unit and prints the evaluation result. The structure evaluation apparatus 20 may include some or all of the display 203, the communication unit, and the printing unit as the output unit and execute the above operations.

The evaluator 202 may display the source distribution as a contour map on the display 203.

A factor causing increase in the number of generated elastic waves is not necessarily limited to the above example (weather phenomenon). More precisely, the numerous micro-objects as the factor causing increase in the number of generated elastic waves are not necessarily limited to objects generated by weather phenomenon. For example, the numerous micro-objects may be objects generated by water-sprinkling by a sprinkler vehicle or spraying or sprinkling chemicals, or by a device such as hammer for hitting. Other hitting may be hitting by chain drawing or by tapping.

The structure evaluation apparatus 20 can control the measurement timing by using a source of elastic waves generated due to an impact generated by artificial actions such as hitting multiple times using a device or micro-objects such as water-sprinkling by a sprinkler vehicle or spraying or sprinkling chemicals. Therefore, diagnosis can be performed more efficiently. If a time of water-sprinkling by a sprinkler vehicle is in advance known, a user of the structure evaluation system 100 starts up the structure evaluation system 100 at the time of water sprinkling by the sprinkler vehicle for evaluation of the structure, thereby controlling the measurement, timing. In this case, because the timing at which elastic waves are generated is known in advance, the structure evaluation system 100 is at rest at normal times, and a trigger for notifying the activation timing may be input from outside in accordance with the timing of generating elastic waves. In this way, operation is possible with reduced power consumption.

To decrease the power required for the measurement, for example, only some of the AE sensors 10 may be activated at normal times, and other AE sensors 10 may be activated when a sharp increase in the number of generated elastic waves is detected. The processing in this case will be described with reference to FIGS. 6 and 7.

Figure 6:
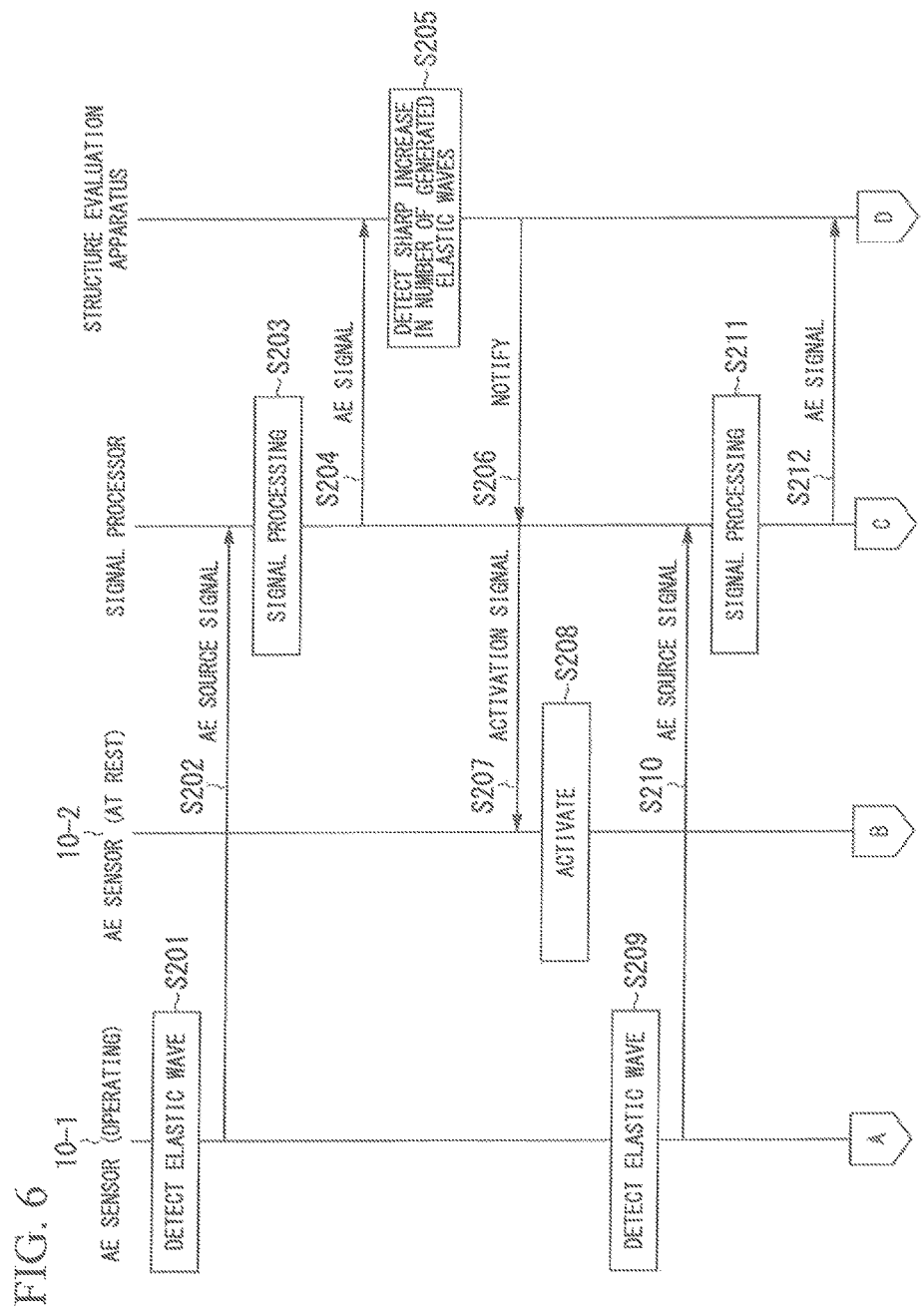
FIG. 6 is a sequence diagram illustrating a processing flow of the structure evaluation system 100.
Figure 7:
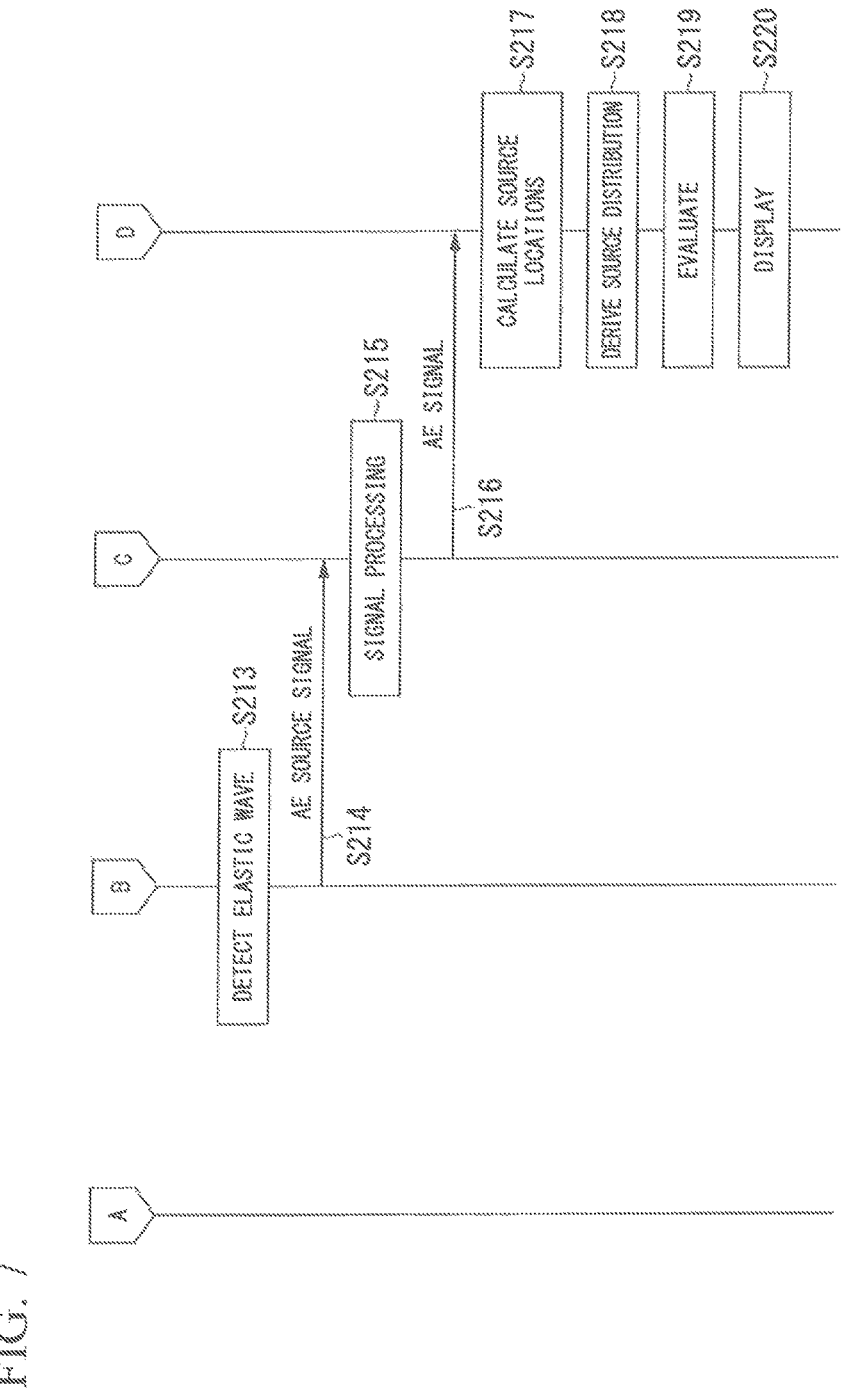
FIG. 7 is a sequence diagram illustrating a processing flow of the structure evaluation system 100.

FIGS. 6 and 7 are sequence diagrams illustrating a processing flow of the structure evaluation system 100. In FIGS. 6 and 7, it is assumed that the AE sensor 10-1 is operating at the start of the processing and the AE sensor 10-2 is at rest. Being at rest does not mean that all functions of the apparatus are paused, but means that only functions related to activation are operating.

The AE sensor 10-1 detects an elastic wave (an AE wave) generated by the structure (Step S201). The AE sensor 10-1 converts the detected elastic wave into a voltage signal (an AE source signal), performs processing, such as amplification, frequency limiting, and the like, on the AE source signal, and outputs the processing result to the signal processor 11 (Step S202). The signal processor 11 performs necessary signal processing such as noise removal and parameter extraction on the input AE source signal (Step S203). The signal processor 11 outputs information based on the AE parameters extracted by performing signal processing to the structure evaluation apparatus 20 as an AE signal (Step S204). The processing from Step S201 to Step S204 is repeatedly executed. The AE signal output from the signal processor 11 is accumulated in the buffer (not illustrated).

It is assumed that the position locator 201 has detected a sharp increase in the number of generated elastic waves (Step S205). For example, the position locator 201 detects that a sharp increase in the number of generated elastic waves has occurred when a difference between the number of elastic waves generated at the current time and the number of elastic waves generated at an immediately preceding time exceeds a third threshold value. The third threshold value may be set in advance or may be appropriately set. Then, the position locator 201 notifies the signal processor 11 that a sharp increase in the number of generated elastic waves has been detected (Step S206). Upon receiving the notification from the position locator 201, the signal processor 11 transmits an activation signal to the AE sensor 10-2 that is at rest (Step S207). The activation signal refers to a signal for instructing execution of activation processing.

Upon receiving the activation signal from the signal processor 11, the AE sensor 10-2 executes the activation processing (Step S208). As a result, the AE sensor 10-2 is operated from the state at rest. The AE sensor 10-1 detects an elastic wave (AE wave) generated by the structure (Step S209). The AE sensor 10-1 converts the detected elastic wave into a voltage signal (AE source signal), performs processing such as amplification and frequency limiting, on the AE source signal, and outputs the processing result to the signal processor 11 (Step S210). The signal processor 11 performs necessary signal processing such as noise removal and parameter extraction on the input AE source signal (Step S211). The signal processor 11 outputs information based on the AE parameters extracted by performing signal processing to the structure evaluation apparatus 20 as an AE signal (Step S212). The processing from Step S209 to Step S212 is repeatedly executed. The AE signal output from the signal processor 11 is stored in the buffer (not illustrated).

The AE sensor 10-2 detects an elastic wave (an AE wave) generated by the structure (Step S213). The AE sensor 10-2 converts the detected elastic wave into a voltage signal (an AE source signal), performs processing, such as amplification, frequency limiting, and the like, on the AE source signal, and outputs the processing result to the signal processor 11 (Step S214). The signal processor 11 performs necessary signal processing such as noise removal and parameter extraction on the input AE source signal (Step S215). The signal processor 11 outputs information based on the AE parameters extracted by performing signal processing to the structure evaluation apparatus 20 as an AE signal (Step S216). The processing from Step S213 to Step S216 is repeatedly executed. The AE signal output from the signal processor 11 is accumulated in the buffer (not illustrated).

The position locator 201 acquires an AE signal within a predetermined period including the target time from the buffer (not illustrated). Using the acquired AE signal, the position locator 201 locates positions of the AE sources (Step S217). Then, the position locator 201 derives the source distribution on the basis of the position location results (Step S218). The position locator 201 outputs the derived source distribution to the evaluator 202. The evaluator 202 performs evaluation using the source distribution output from the position locator 201 (Step S219). The evaluation method is the same as the above-mentioned method and will thus be omitted. The evaluator 202 makes the display 203 display the evaluation result. The display 203 displays the evaluation result according to the control of the evaluator 202 (Step S220).

By the above constitution, it is not always necessary for ah the AE sensors 10 to be in operation. Thus, power consumption can be reduced.

Further, when some or ail of the AE sensors 10 are at rest, the AE sensor 10 may be activated when a micro-object is detected by a device such as a rain gauge, a camera, and a microphone. Also, for example, the AE sensor 10 may be activated at a time when an event due to an impact on a structure is expected based on weather information such as rainfall, temperature and humidity levels near a measurement region.

According to at least one of the embodiments described above, a structure can be evaluated efficiently by having the plurality of AE sensors 10 configured to detect elastic waves generated from a structure, the signal processor 11 configured to perform signal processing on the elastic waves detected by the AE sensors 10 to output an AE signal, a position locator 201 configured to derive a source distribution by using an AE signal caused by an impact on the structure, and the evaluator 202 configured to evaluate a state of deterioration of a predetermined region of the structure from a density of AE sources obtained on the basis of the source distribution.

Although a few embodiments of the present invention have been described above, the embodiments are merely examples are not intended to limit the scope of the invention. The embodiments may be implemented in various other forms, and various omissions, substitutions, and changes can be made to the embodiments within the scope not departing from the gist of the invention. The embodiments and modifications thereof belong to the claims below and their equivalents as well as the scope and gist of the invention.

REFERENCE SIGNS LIST 10 (10-1 to 10-n) AE sensor
11 Signal processor
20 Structure evaluation apparatus
201 Position locator
202 Evaluator
203 Display

The invention claimed is:

1. A structure evaluation system comprising:
   a plurality of sensors configured to detect an elastic wave generated from a structure;
   a signal processor configured to perform noise removal of the elastic wave;
   a position locator configured to derive a source distribution of the elastic waves generated from the structure, caused by an impact on the structure; and
   an evaluator configured to evaluate a state of deterioration of the structure from characteristic parameters of the elastic waves in the source distribution,
   wherein characteristic parameters of the elastic waves is a density of the elastic waves, and
   wherein the evaluator evaluates a region in which the density of the elastic waves is less than a first threshold value as a region in which deterioration of the structure is occurring.

2. The structure evaluation system according to claim 1, wherein the position locator derives the source distribution by using, as a signal of the elastic waves generated from the impact on the structure, a signal obtained from the elastic waves at a time at which the number of detected elastic waves is a second threshold value or larger or a signal obtained from the elastic waves within a predetermined period including the time.

3. The structure evaluation system according to claim 1, wherein the impact on the structure is an impact generated due to colliding of numerous micro-objects.

4. The structure evaluation system according to claim 3, wherein the micro-objects are objects generated by weather phenomena.

5. The structure evaluation system according to claim 3, wherein the impact generated due to colliding of the micro-objects is an impact generated by artificial actions.

6. The structure evaluation system according to claim 3, wherein the impact generated due to colliding of the micro-objects is an impact applied to a surface opposite to a surface at which the sensors are installed.

7. The structure evaluation system according to claim 1, wherein the micro-objects are objects which provide influence to the structure from the outside of the structure.

8. The structure evaluation system according to claim 1, further comprising:
   a signal processor that activates sensors at rest among the sensors when the number of detected elastic waves is a third threshold value or larger, wherein the sensors at rest are part of the sensors.

9. The structure evaluation system according to claim 1, further comprising:
   a signal processor that activates a sensor or sensors at rest among the sensors at a time when an event due to an impact on the structure is expected, wherein the sensor or sensors at rest are part or all of the sensors.

10. A structure evaluation method comprising:
    a signal processing step of performing noise removal of the elastic wave;
    a position locating step of deriving a source distribution of elastic waves generated from a structure, caused by an impact on the structure; and
    an evaluating step of deriving a state of deterioration of the structure from characteristic parameters of the elastic waves in the source distribution, wherein characteristic parameters of the elastic waves is a density of the elastic waves, and wherein the evaluating step evaluates a region in which the density of the elastic waves is less than a first threshold value as a region in which deterioration of the structure is occurring.

11. A structure evaluation system comprising:

a plurality of sensors configured to detect an elastic wave generated from a structure;

a signal processor configured to activate a sensor or sensors at rest when the condition is satisfied, wherein the sensor or sensors at rest are a part or all of the plurality of sensors, wherein the condition is any one when the number of detected elastic waves is a third threshold value or larger or when an event due to an impact on the structure is expected or when a trigger for notifying activation is input from the outside of the structure;

a position locator configured to derive a source distribution of the elastic waves generated from the structure, caused by an impact on the structure; and an evaluator configured to evaluate a state of deterioration of the structure from characteristic parameters of the elastic waves in the source distribution, wherein characteristic parameters of the elastic waves is a density of the elastic waves, and wherein the evaluator evaluates a region in which the density of the elastic waves is less than a first threshold value as a region in which deterioration of the structure is occurring.

12. A structure evaluation method comprising:

a signal processing step of activating a sensor or sensors at rest when the condition is satisfied, wherein the sensor or sensors at rest are a part or all of the plurality of sensors, wherein the condition is any one when the number of detected elastic waves is a third threshold value or larger or when an event due to an impact on the structure is expected or when a trigger for notifying activation is input from the outside of the structure;

a position locating step of deriving a source distribution of elastic waves generated from a structure, caused by an impact on the structure; and an evaluating step of deriving a state of deterioration of the structure from characteristic parameters of the elastic waves in the source distribution, wherein characteristic parameters of the elastic waves is a density of the elastic waves, and wherein the evaluating step evaluates a region in which the density of the elastic waves is less than a first threshold value as a region in which deterioration of the structure is occurring.

* * * * *